United States Patent
Hillebrand et al.

(10) Patent No.: US 11,702,648 B2
(45) Date of Patent: Jul. 18, 2023

(54) PROCESS FOR CONCENTRATING CELLS FROM A SAMPLE AND THEN ISOLATING NUCLEIC ACIDS FROM SAID CELLS

(71) Applicant: IST Innuscreen GmbH, Berlin (DE)

(72) Inventors: Timo Hillebrand, Hoppegarten (DE); Monique Brendel, Bucha (DE); Kristin Wessel, Buergel (DE)

(73) Assignee: IST Innuscreen GmbH, Berlin (DE)

( * ) Notice: Subject to any disclaimer, the term of this patent is extended or adjusted under 35 U.S.C. 154(b) by 797 days.

(21) Appl. No.: 16/493,450

(22) PCT Filed: Mar. 14, 2018

(86) PCT No.: PCT/EP2018/056371
§ 371 (c)(1),
(2) Date: Apr. 21, 2020

(87) PCT Pub. No.: WO2018/167138
PCT Pub. Date: Sep. 20, 2018

(65) Prior Publication Data
US 2020/0255820 A1  Aug. 13, 2020

(30) Foreign Application Priority Data

Mar. 14, 2017 (DE) .................... 10 2017 204 267.2

(51) Int. Cl.
*C12N 15/10* (2006.01)
*B01J 20/28* (2006.01)

(52) U.S. Cl.
CPC .... *C12N 15/1006* (2013.01); *B01J 20/28054* (2013.01)

(58) Field of Classification Search
CPC ........................ C12N 15/1006; B01J 20/28054
See application file for complete search history.

(56) References Cited

U.S. PATENT DOCUMENTS

| | | | |
|---|---|---|---|
| 5,234,809 A | 8/1993 | Boom et al. | |
| 6,383,393 B1 | 5/2002 | Colpan et al. | |
| 6,699,987 B2 | 3/2004 | Hillebrand et al. | |
| 7,776,580 B2 | 8/2010 | Zhang et al. | |
| 7,964,364 B2 | 6/2011 | Refseth et al. | |
| 8,247,545 B1 | 8/2012 | Colpan | |
| 2018/0133710 A1 | 5/2018 | Hillebrand et al. | |
| 2018/0148712 A1 | 5/2018 | Hillebrand et al. | |
| 2018/0148766 A1 | 5/2018 | Hillebrand et al. | |
| 2018/0327827 A1 | 11/2018 | Han et al. | |

FOREIGN PATENT DOCUMENTS

| | | |
|---|---|---|
| DE | 41 39 664 | 6/1993 |
| DE | 4321904 | 1/1995 |
| DE | 10 2010 031 401 | 1/2012 |
| DE | 10 2015 216 558 | 10/2016 |
| DE | 10 2015 211 393 | 12/2016 |
| DE | 10 2015 211 394 | 12/2016 |
| EP | 1135479 | 9/2001 |
| EP | 3 056 565 | 8/2016 |
| WO | 95/34569 | 12/1995 |
| WO | 00/34463 | 6/2000 |
| WO | 01/05510 | 1/2001 |
| WO | 01/53525 | 7/2001 |
| WO | 2004/053115 | 6/2004 |
| WO | 2016/169679 | 10/2016 |
| WO | 2017/039286 | 3/2017 |

OTHER PUBLICATIONS

Kim et al., Small, 2016, 12(2), p. 190-197, Published online: Nov. 16, 2015. (Year: 2015).*
Assal et al., Transfusion, 2009, 49, p. 289-300. (Year: 2009).*
Gupte, S.C., Asian Journal of Transfusion Science, 2015, vol. 9 Supplement 1, p. S6-S10. (Year: 2015).*
Morgenthaler et al., Vox Sang., 1985, 48, p. 8-17. (Year: 1985).*
Robert et al., Lab Chip, 2011, 11, p. 1902-1910. (Year: 2011).*
International Search Report dated May 28, 2018 in PCT/EP2018/056371 with English translation.
Written Opinion dated May 28, 2018 in PCT/EP2018/056371.
Šafařík et al., "Use of magnetic techniques for the isolation of cells," Journal of Chromatography B, 722 (1999) 33-53 XP004156204, DOI: 10.1016/S0378-4347(98)00338-7.
Keil University, "Oberflächenstrukturen", Attempt No. M402, available at: https://www.tf.unikiel.de/matwis/amat/semitech_en/kap_3/illustr/oberflaechenstrukture.pdf, Mar. 28, 2007, pp. 1-12.

* cited by examiner

*Primary Examiner* — Jonathan S Lau
(74) *Attorney, Agent, or Firm* — Grüneberg and Myers, PLLC

(57) ABSTRACT

Biological cells are concentrated and isolated from a sample and/or biological cells are concentrated from a sample, followed by the isolation of nucleic acids from said cells. The sample is brought into contact with a solid phase which has a rough or structured surface.

13 Claims, 1 Drawing Sheet

1    2    3    4

1  2  3  4  5  6  7  8  9

PROCESS FOR CONCENTRATING CELLS FROM A SAMPLE AND THEN ISOLATING NUCLEIC ACIDS FROM SAID CELLS

CROSS-REFERENCE TO RELATED APPLICATIONS

This application is a National Stage entry under § 371 of International Application No. PCT/EP2018/056371, filed on Mar. 14, 2018, and which claims the benefit of German Application No. 10 2017 204 267.2, filed on Mar. 14, 2017, the contents of each of which are hereby incorporated by reference in their entireties.

BACKGROUND OF THE INVENTION

Field of the Invention

Subject matter of the invention is a novel and greatly simplified method permitting concentrating biological cells from a sample, and removing them from the sample, then releasing and isolating the nucleic acids contained in the cells in such a manner that the same means used for concentrating the cells is also used for isolating the nucleic acids.

Discussion of the Background

The method can be carried out manually or fully automatically. It simplifies in particular the isolation of nucleic acids from larger sample volumes and in this connection also reduces use of necessary extraction reagents.

Under conventional conditions, the isolation of DNA from cells and tissues occurs by starting materials containing nucleic acids being opened up under strongly denaturing and reducing conditions, partly also by utilizing enzymes decomposing protein, and by cleaning the emerging nucleic acid fractions through phenol/chloroform extraction steps, and by obtaining the nucleic acids by means of dialysis or ethanol precipitation from the aqueous phase (Sambrook, J., Fritsch, E. F. and Maniatis, T., 1989, CSH, "Molecular Cloning").

These "conventional methods" for isolating nucleic acids from cells and in particular from tissues are very time-consuming (partly longer than 48 hours), require extensive technical equipment, and moreover cannot be realised under field conditions. In addition, such methods are hazardous to health in no small degree due to the chemicals used such as phenol and chloroform.

The conventional methods for isolating nucleic acids have been clearly improved during the past years. The "new" methods are based on a method developed and described for the first time by Vogelstein and Gillespie (Proc. Natl. Acad. Sci. USA, 1979, 76, 615-619) for preparative and analytical cleaning of DNA fragments from agarose gels. The method combines dissolution of an agarose containing the DNA bands to be isolated in a saturated solution of a chaotropic salt (NaJ) with binding of the DNA to glass particles. The DNA fixed to the glass particles is subsequently washed by means of a washing solution (20 mM Tris HCl [pH 7.2]; 200 mM NaCl; 2 mM EDTA; 50% v/v ethanol) and then detached from the carrier particles.

Said method until today has been modified frequently, and is presently applied to different methods of extraction and cleaning of nucleic acids from various origins (Marko, M. A., Chipperfield, R. and Birnboim, H. G., 1982, Anal. Biochem., 121, 382-387).

Beyond it, today also a large number of reagent systems exists worldwide for cleaning DNA fragments from agarose gels, and for isolating plasmid DNA from bacterial lysates but also for isolating longer-chained nucleic acids (genomic DNA, cellular total RNA) from blood, tissues or cell cultures as well.

All these commercially available kits are based upon the sufficiently known principle of binding nucleic acids to mineral carriers under the presence of solutions of different chaotropic salts and use as carrier materials suspensions of finely ground glass powders (e.g. Glasmilk, BIO 101, La Jolla, Calif.), diatomaceous earth (Sigma) or silica gels (Diagen, DE 41 39 664 A1) as well.

A workable method for a variety of different applications for isolating nucleic acids is shown in U.S. Pat. No. 5,234,809 (Boom) where a method for isolating nucleic acids from nucleic acid containing starting materials by incubation of the starting material with a chaotropic buffer and a DNA binding solid phase is described. The chaotropic buffers realize not only the lysis of the starting material but also binding of the nucleic acids to the solid phase. The method is well suited for isolating nucleic acids from small sample quantities and is applied in practice especially in the field of isolating viral nucleic acids.

Specific modifications of these methods relate to the use of novel carrier materials showing practical advantages for certain tasks (WO-A 95/34569). Further improved extraction methods relate to the use of novel lysis/binding buffers.

Patent specification EP 1135479 discloses that for adsorption of nucleic acids to the siliceous materials known and used by those skilled in the art, also so-called anti-chaotropic salts as a component of lysis/binding buffer systems can be used very efficiently and successfully. The advantage of this method is that by bypassing the use of chaotropic salts, a clearly lower health hazard emanates from the extraction systems. But for an efficient isolation of nucleic acids from a complex biological sample, in particular in view of a nucleic acid production with a yield as high as possible, high salt concentrations (>1.5 M) are required in turn in the lysis buffer. Hence, the patent specification discloses that the lysis buffers used contain salt concentrations between 1.5 M-3 M. In the patent specification DE 4321904, a method is described that when combining chaotropic high-salt buffers with alcoholic components, an efficient isolation of nucleic acids is possible.

Analysis of prior art impressively shows that a large number of possibilities exists for binding nucleic acids to solid carrier materials, in particular mineral carrier materials on silicon basis, but also to magnetic or paramagnetic siliceous carrier materials and/or magnetic or paramagnetic materials carrying functional groups corresponding to the same function as siliceous materials, washing them subsequently, and removing the nucleic acids from the carrier material again. In this connection, the materials exist as membranes (and/or glass fiber mats) and/or in the form of micro or nano materials. For providing binding of the nucleic acids to the carrier materials, not only so-called chaotropic salts but also so-called anti-chaotropic salts or mixtures out of these are used. Independent of the mineral carrier materials used for binding nucleic acids, all these methods work according to the same process sequence:
1. lysis of the sample
2. optional addition of the binding buffer necessary for binding the nucleic acid
3. contacting the reaction batch with a nucleic acid binding solid phase (carrier material) and subsequent binding the nucleic acid to said material 4. washing the nucleic acid bound to the carrier material
5. removing the nucleic acid bound from the carrier material The State of the Art discloses that methods for isolating nucleic acids from small volume samples work very efficiently. But if large sample volumes are to be processed, these methods clearly lose efficiency, and moreover become increasingly complicated and elaborate in their implementation. This relates in particular to isolating nucleic acids from whole blood samples.

One alternative solution for isolating DNA from larger blood volumes (>200 µl) is based on the fact that a larger volume of lysis buffer is added to the sample in the usual manner, subsequently a binding buffer is added, and the preparation is lead, for example, by means of a "hopper device", successively through a filter membrane for binding the nucleic acid. Such commercially available kits permit to use samples of more than 1 ml for isolating nucleic acid. But these methods require a clearly higher proportion of extraction reagents and are elaborate in implementation.

Another widely used alternative solution for isolating nucleic acids from large volume blood samples is based on the fact that in first process steps the erythrocytes are selectively destroyed, and the nucleated cells are then pelletized by means of centrifugation which drastically reduces the sample volume. Further processing occurs with the nucleated cells obtained. The disadvantage of such a method are the process steps of lysis of the erythrocytes and pelletizing of the nucleated cells to be carried out. For automatisation of these steps, a centrifuge is required. It is known that technical implementation of a centrifuge into an automated process for isolating nucleic acids is elaborate and expensive.

Further possibilities for processing larger sample volumes with the objective of isolating nucleic acids, especially from pathogenic microorganisms are based on the use of so-called immunomagnetic methods. These methods are based on the use of, for example, magnetic beads which are coupled to a captor molecule (for example with a target specific antibody). These beads are brought into contact with the biological sample, and incubated for several hours. During this process, the target is supposed to specifically bind to the antibody. Subsequently, the beads are separated and washed. Then the bound targets are removed. In the case of planned isolation of nucleic acids from the bound analytes, the bound analyte is lysed, and subsequently a known nucleic acid isolation is performed.

These methods are elaborate and extremely expensive because they are always based on the use of antibodies coupled to magnetic beads. Moreover, such methods are not robust either because the beads with the coupled antibodies must always be cooled. Another method to this effect can be found in the Journal of Virology (Vol. 83, No. 10; 2009). This is the immunomagnetic concentration of virus antigen in urine samples wherein 1.5 ml sample can be used. The method uses magnetic beads which are coupled to a protein (ApoH). These beads serve for binding the virus antigen from the sample. The incubation of the sample with beads is 2 hours. Subsequently, the beads are separated and washed several times. Then the lysis of the viruses occurs by means of a lysis buffer. The lysis buffer is then put on a filter column, and the nucleic acid is bound, washed on the filter column in a known manner, and then the viral nucleic acid is isolated. This method as well is again expensive and elaborate in processing.

These methods show that it is possible to process larger sample volumes. But it is revealed as well that the concentration of cells and isolation of nucleic acids from these cells are two separate process sequences, and that the means, which are used for concentration of the cells, cannot be used for isolation of the nucleic acids.

Patent specification U.S. Pat. No. 7,964,364 discloses a different method. Here, it is described that cells from a sample bind to a solid phase wherein said solid phase is provided with a non-specific captor ligand. This coating consists of carbohydrates and/or carbohydrate derivatives. Preferably, microorganisms are binding. The solid phase are magnetic particles. After binding, the solid phase is removed from the sample, and the cells are lysed. Subsequently, the conditions are set so that the nucleic acid released can bind to the magnetic particles. After washing steps, the DNA is eluted. Thus, the surface modified magnetic particles on the one hand serve for adsorption of cells from a sample and subsequently for isolation of the nucleic acid from the cells separated before. The methods and means disclosed in the patent specification U.S. Pat. No. 7,776,580 as well as in the unexamined application DE 10 2010 031 401 are similar. Cells or cellular components are bound to magnetic particles and separated from the sample, the cells are lysed and the released nucleic acid is bound to the same magnetic particles and subsequently isolated. The extraction chemistry used for binding the nucleic acids and/or isolating the nucleic acids corresponds again precisely to the State of the Art. Hence, these methods are an improvement since the particle used for cell binding in another function also permits isolation of nucleic acids of the bound and separated cells. But disadvantageous is the use of magnetic particles. Since these are solely nano- and/or microparticles, separation of these particles is difficult, and in particular for viscous particles very time-consuming.

Thus, these methods become elaborate and always require a hardware solution which permits a magnetic separation. Moreover, it turns out that magnetic micro- and/or nanoparticles have only a very limited binding capacity for nucleic acids. In addition, the surfaces of the particles must often still be chemically modified which involves an additional effort with respect to time and cost. It is very important to mention as well that possible considerable health risks emanate from nanomaterials.

SUMMARY OF THE INVENTION

The present invention solves the problem of combined concentration of cells and subsequent isolation of nucleic acids in a surprisingly simple manner.

The invention was based on the following surprising observation. If a sample containing cells (for example, a blood sample) is brought into contact with a plastic material with a rough surface (for example, roughened polypropylene), the cells bind to the plastic material. No captor ligands exist on the material, as this is known from the State of the Art.

The term "rough surface" is to be understood in such a manner that by touching or viewing the surface it can be recognized that the surface is not smooth. This may as well be a surface which has a structure (for example, grooves). By this structure, the smoothness of the surface is eliminated, even if the structure, hence the grooves, themselves can be smooth. According to the invention, such surfaces are called "structured surfaces". If by viewing or touching of the surface it cannot be recognized whether a surface is smooth or rough, a test can be made in which a laser beam is directed on said surface. In the case of a smooth surface, the laser is reflected only in the main direction on the surface. In the case of rough surfaces, a scattering in all spatial directions occurs. Such a test has been described on the website of Kiel University (www.tf uni-kiel.de/matwis/amat/semitech_en/kap 3/illustr/oberflaechen-strukture.pdf).

For a person skilled in the art it is easy to find out as to whether a surface has the necessary roughness for a binding of cells and/or nucleic acids. He or she must only carry out a corresponding test with the surface to be examined by bringing an aqueous solution with biological cells into contact with said surface and checking as to whether the cells are being bound.

After the fixation of the cells onto the surface has been made, the cells can be removed from the sample with the surface.

DETAILED DESCRIPTION OF THE INVENTION

Figure 1:
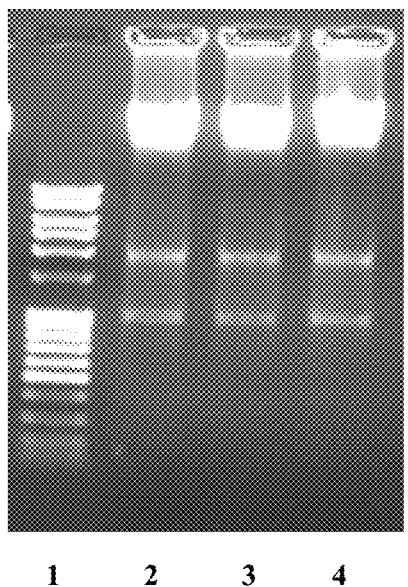
FIG. 1 shows an analysis by gel electrophoresis of the isolated nucleic acid for Example 1.

The objective of the invention, namely isolation of the nucleic acids contained in the fixed cells, by using the same means, is achieved by the fact that the cells are lysed by means of a lysis buffer and thus releases the nucleic acids. After release of the nucleic acids, these can also be isolated with the same surface which has been used for fixation of the cells.

Here, the method according to the invention combines for the first time the adsorption of cells of a sample to a material with a "structured surface" with subsequent isolation and purification of nucleic acids by using the same surface. Here, the method can be carried out as a single tube process or also in the form of an automated "walk-away-method". The carrier material used with a "structured surface" is cost-effective and non-hazardous contrary to nanoparticles used.

There is no actual limitation of the method with respect to the volume of the sample nor with respect to the type of sample. Precisely the last point has a crucial advantage since with it also samples can be efficiently processed, which, with the known methods of the nucleic acid isolation, can only be processed in a complex manner, in particular samples with a high inhibitory potential. The advantage is based on the method according to the invention. In the first process step, the cells from a sample are adsorbed to the "structured" or rough surface. Hence, the sample can be discarded, and in this connection also the inhibitory matrix components. Moreover, the cells located on the "structured surface" can also be washed with water. For subsequent nucleic acid isolation, clean cells are then already available. Among others, this is also important when isolating DNA from blood samples.

The process sequence is simple, extremely rapid and very efficient and combines according to the invention a concentration of cells with the subsequent extraction of the nucleic acid. The invention bears reference to the disclosed methods and means of the specifications DE 10 2015 216 558, DE 10 2015 211 394 and DE 10 2015 211 393. The invention is based on the properties described there that nucleic acids can be isolated on rough and/or "structured surfaces". Surprisingly, the present invention shows that such a material is not only suitable for isolating nucleic acids but is also suitable for binding cells from a sample. Thus, the process approach according to the invention results that such a material can be used in a combined manner in dual function.

Hence, the gist of the invention is that cells of a sample adsorb to a "structured surface", and subsequently the nucleic acids released by the lysis are to be found in an aqueous environment, the polarity of which is set by means of organic substances such that solubility of the nucleic acid is reduced and subsequently precipitates on the "structured surface", and then the precipitated DNA is detached again from the "structured" rough surface, and is available. Optionally, the nucleic acid precipitated on the rough surface can also be washed and be detached after the washing steps.

The method is extremely simple and rapid in implementation. Generally, it can be carried out in the following steps:

1. Contacting a sample, which contains cells, with a material with a "structured surface" and subsequent adsorption of the cells contained in the sample to said surface. If required, a solution containing calcium chloride is added to the sample in addition. This can even increase efficiency of the adsorption of cells. Removal of the surface from the sample and, if required, washing of the adsorbed cells on the surface.
2. Lysing cells with a lysis buffer. Said lysis buffer can contain chaotropic salts or non-chaotropic salts or mixtures of these two groups. Moreover, said buffer can contain other components such as chelating agents, Tris buffers, wetting agents and dispersing agents etc. But the method also works with buffers, which do not contain any salts, and are, for example, only composed of a detergent, Tris and EDTA. In addition, also proteolytic enzymes can be used.
3. Addition of a binding buffer, which contains an alcoholic component and other additives or addition of an alcohol alone or also addition of acetone or benzine. Thus, the nucleic acid of the sample precipitates on the same structured surface to which the cells have been adsorbed before.
4. If required, washing and subsequent drying of the "structured surface".
5. Final detaching of the nucleic acid from the material with an elution buffer (low salt buffer or water).

All these process steps from cell adsorption, lysis of cells, binding of nucleic acids, washing of bound nucleic acids and final detaching of the nucleic acids occur by the fact that the "structured surface" is brought into contact with the respective components by agitating or pipetting.

The method is universally applicable and can be carried out not only in an automated manner but also manually.

Preferably, in particular for an automated operation by using any liquid handling station, the means according to the invention can also be located in a device for extraction of nucleic acids, comprising a hollow body through which a liquid is passed, wherein in said hollow body a material with rough or "structured surface" is located in such a manner that a liquid can flow around it. In a preferred embodiment, a pipette tip acts as a hollow body. The material with rough or "structured surface" has such a size that it cannot exit the pipette tip at the bottom and thus differs from the magnetic particles described in the State of the Art (WO 01/05510 A1). In summary it is necessary that within the pipette tip a two-/three-dimensional structure is created by the material introduced to which at first cells and subsequently after lysis of the cells the nucleic acids released can adsorb.

The materials to be used, which have been introduced into the pipette tip, for cell adsorption and subsequent binding of nucleic acids can be extremely different. Modified plastic materials can be used, the surface of which is not smooth but rough or structured. This includes also so-called composite materials which are mixtures from polymers and, for example, organic components as well as inorganic components. Important is only the provision of a roughened and/or "structured surface" (no smooth surface) and/or putting material into the pipette tip leading to the formation of a two-/three-dimensional network with the nucleic acids precipitating then on said structure. Architecture of the material is likewise not limiting (round, rectangular etc.). Also several materials can be used (for example, several granules).

It is important that a liquid can flow at any time around the material, which is put into a pipette tip, without it being necessary that the liquid must pass through the material introduced. Also, a pipette tip can be used which (made from an injection-molded part) already contains the binding material, and which must no longer be put into the tip. It is also advantageous to use rough or structured material having in addition magnetic or paramagnetic properties. Such a material is then also suitable for manual sample processing where it is put separately into the sample and is not in a hollow body.

The sample with the cells contained in the sample is "pipetted past" the material according to the invention put in the pipette tip by means of pipetting operations. The cells adsorb to the material. In a preferred embodiment, calcium chloride can still be added to the sample containing the cells. This seems to accelerate and/or enhance the efficiency of cell adhesion to the material according to the invention. After cell adhesion, the pipette tip is immersed into a cavity in which there is a lysis buffer and, if appropriate, also a proteolytic enzyme. Now, lysis of the cells and release of the nucleic acids occurs. Thus, the cells are no longer on the material according to the invention. Now, according to the invention, the subsequent process steps serve for binding the released nucleic acids to the same material according to the invention on which the cells had been before. After the lysis of the cells has been carried out, the nucleic acid to be isolated is in aqueous form. Subsequently, the conditions required for precipitation of the nucleic acids are adjusted so that the nucleic acid can precipitate on the material put into the pipette tips. The batch is "pipetted past" the nucleic acid binding material which has been put vertically in the pipette tip through pipetting operations. The nucleic acids precipitate on the material. Subsequently, washing buffers can optionally be "pipetted past" the nucleic acid binding material as well. Then, a drying step occurs (for example, frequent pipetting and pipetting off). Finally, the eluent is in turn "pipetted past" the vertically disposed nucleic acid binding material several times, and the bound nucleic acid is detached in the process. Now, the nucleic acid is available for a necessary downstream application. The method is extremely rapid and simple in implementation and permits isolating nucleic acids in an extremely high yield and purity.

Apart from the simplicity of implementation, the present invention has another huge advantage. If a biological sample contains large quantities of nucleic acid containing cells, an extremely high quantity of nucleic acids can be extracted by means of the method according to the invention and the materials according to the invention. Thus, the method is also ideally suitable for processing large sample volumes.

The invention will be explained in detail below by means of embodiments while the embodiments do not constitute a limitation of the invention.

EXAMPLES

Example 1: Concentration of Cells from an Aqueous Solution Combined with the Subsequent Extraction of the Nucleic Acid Contained in the Cells by Using a Modified Pipette Tip as Well as by Using a Commercially Available Automated Extraction System Automated extraction has been carried out by means of the InnuPure C16 automated extraction system (Analytik Jena AG).

For the implementation of a nucleic acid extraction pursuant to the method according to the invention, the pipette tips have been modified in such a manner that they correspond to the means according to the invention. Napped plastic granules (4 granules with a diameter of approx. 2 mm to 4 mm; polypropylene) have been loosely introduced vertically into the lower third of the pipette tips wherein the granules do not close the lumen of the pipette tip so that the pipetting function of the pipette tips is maintained.

The method according to the invention has then been carried out on the automated InnuPure C16 system as follows:

The reagents required for the process existed in a pre-filled deepwell plate. The aqueous cell suspension has been put into the first cavity.

The pipette tip with the material according to the invention has been introduced into the cavity. Cell binding occurs by pipetting and pipetting off (100 repetitions). In this process, the cells adsorb to the material according to the invention contained in the tip. After termination of the pipetting operation, the tip has been extracted from the cavity. The cells are on the material within the tip. Subsequently, the tip has been introduced into a second cavity of the deepwell plate. A commercially available lysis buffer as well as proteinase K (LysisSolution CBV; innuPREP Blood DNA Kit/IPC16; Analytik Jena AG) are located in this cavity. Lysis of the cells located on the material occurred by pipetting and pipetting off of the lysis buffer (200 repetitions). The cavity has been heated in addition. At the end of the operation, the released nucleic acid of the cells is in the lysis buffer. The cells are no longer on the material according to the invention. The sample has now been put into the pipette tip and released into another cavity of the deepwell plate. This cavity is pre-filled with an alcohol (isopropanol).

Subsequently this solution has again been pipetted and pipetted off by means of the pipette tip again in such a manner that the solution is flowing past the granules (100 repetitions). Now, the binding of the released nucleic acid to the material according to the invention occurred with which the cells had already been adsorbed from the sample before. After binding of the nucleic acid to the granules, the washing steps still occurred.

For this, 3 further cavities of the deepwell plate have been filled with an alcoholic washing buffer. Washing occurred by pipetting and pipetting off of the washing buffers (10 repetitions each time).

After the last washing step, the tip according to the invention and the granules contained therein has been dried by pipetting air and thus the remaining ethanol has been removed. Elution of the nucleic acids from the granules occurred in another cavity of the deepwell plate in which 200 µl water were contained as an eluent. The nucleic acid has been detached from the granules by pipetting and pipetting off of the water (120 repetitions).

The method is extremely simple and rapid and shows that commercially available automated extraction systems for carrying out the process according to the invention in the combination of cell binding and removal of cells from the initial sample and subsequent extraction of the nucleic acid contained in the cells can be used in combination with the corresponding means according to the invention.

Proof of the isolated nucleic acid occurs by means of spectrophotometric measurement and gel electrophoresis.

Results of the Spectrophotometric Measurement

| Sample | Concentration (ng/μl) | Yield (μg) | Ratio $A_{260}:A_{280}$ | Ratio $A_{260}:A_{230}$ |
|---|---|---|---|---|
| aqueous cell suspension sample 1 approx. $2 \times 10^6$ NIH 3T3 cells | 182 | 38.4 | 1.8 | 2.3 |
| aqueous cell suspension sample 1 approx. $2 \times 10^6$ NIH 3T3 cells | 161 | 32.2 | 1.9 | 2.3 |
| aqueous cell suspension sample 1 approx. $2 \times 10^6$ NIH 3T3 cells | 178 | 35.6 | 1.8 | 2.3 |

An analysis by gel electrophoresis of the isolated nucleic acid is shown in FIG. 1.

The nucleic acid separated by electrophoresis in an 0.8% agarose gel is shown which has been isolated by means of the method according to the invention. The samples have been plotted from left to right, starting with sample 1. Track 1 contains a DNA conductor.

Example 2: Concentration of Nucleated Cells from Different Volumes of Whole Blood Samples Combined with Subsequent Extraction of the Nucleic Acid Contained in the Nucleated Cells by Using a Modified Pipette Tip as Well as by Using a Commercially Available Automated Extraction System Automated extraction has again been carried out by the InnuPure C16 (Analytik Jena AG) automated extraction system. For carrying out a nucleic acid extraction pursuant to the extraction method according to the invention, the pipette tips have been modified in such a manner that they correspond to the means according to the invention. Napped plastic granules (4 granules with a diameter of approx. 2 mm to 4 mm; polypropylene) have been loosely introduced vertically into the lower third of the pipette tips so that the pipetting function of the pipette tips is maintained.

The method according to the invention has then been realised on the automated InnuPure C16 system as follows.

The reagents required for the method existed in a pre-filled deepwell plate. Different blood quantities (200 μl, 300 μl, 400 μl and 500 μl) have been put into the first cavity. 800 μl each of a commercially available erythrocytes lysis buffer (Ery Lysis Solution A; Analytik Jena AG) have been added to these blood samples. Moreover, still 200 μl of a 1 M calcium chloride solution were still added.

The pipette tip with the material according to the invention has been introduced into the cavity. Cell binding occurs by pipetting and pipetting off (100 repetitions). During this process, the nucleated cells adsorb the nucleated cells to the material according to the invention contained in the tip. After termination of the pipetting operation, the tip has been extracted from the cavity. The cells are on the material within the tip. By this, the cells were separated from the actual sample and thus also from inhibitory substances such as hemoglobin. This considerably facilitates the subsequent successful extraction of the nucleic acid. The tip has been subsequently introduced into a second cavity of the deepwell plate. A commercially available lysis buffer as well as proteinase K (LysisSolution CBV; innuPREP Blood DNA Kit/IPC16; Analytik Jena AG) are located in this cavity. Lysis of the cells located on the material occurred by pipetting and pipetting off of the lysis buffer (200 repetitions). The cavity has been heated in addition. At the end of the operation, the released nucleic acid of the cells is in the lysis buffer. The cells are no longer on the material according to the invention. The sample has now been put into the pipette tip and released into another cavity of the deepwell plate. This cavity is pre-filled with an alcohol (isopropanol)

Subsequently, this solution has again been pipetted and pipetted off by means of the pipette tip in such a manner that the solution is flowing past the material filled in (100 repetitions). Now, the binding of the released nucleic acid to the material according to the invention occurred with which the cells had already been adsorbed before from the sample. After binding the nucleic acid to the granules, the washing steps still occurred.

For this, 3 further cavities of the deepwell plate have been filled with an alcoholic washing buffer. Washing occurred by pipetting and pipetting off of the washing buffers (10 repetitions each time).

After the last washing step, the tip according to the invention and the material contained therein has been dried by pipetting air and thus the remaining ethanol has been removed. Elution of the nucleic acids from the granules occurred in another cavity of the deepwell plate in which 200 μl water were contained as an eluent. The nucleic acid has been detached from the granules by pipetting and pipetting off of the water (120 repetitions).

Proof of the isolated nucleic acid occurred by means of spectrophotometric measurement and gel electrophoresis. It turns out that by the increase of the blood quantity also the yield of nucleic acid increases. Thus, the method is also excellently suitable for processing larger sample volumes.

Results of the Spectrophotometric Measurement

| Sample | Concentration (ng/μl) | Yield (μg) | Ratio $A_{260}:A_{280}$ | Ratio $A_{260}:A_{230}$ |
|---|---|---|---|---|
| blood sample 1 (200 μl) | 30 | 6.0 | 1.7 | 1.9 |
| blood sample 1 (200 μl) | 26 | 5.2 | 1.7 | 2.1 |
| blood sample 1 (300 μl) | 40 | 8.0 | 1.7 | 2.3 |
| blood sample 1 (300 μl) | 51.5 | 10.3 | 1.7 | 2.3 |
| blood sample 1 (400 μl) | 72.5 | 14.5 | 1.7 | 2.3 |
| blood sample 1 (400 μl) | 58 | 11.6 | 1.7 | 2.2 |
| blood sample 1 (500 μl) | 75.5 | 15.1 | 1.7 | 2.1 |
| blood sample 1 (500 μl) | 69.5 | 12.9 | 1.7 | 2.1 |

Figure 2:
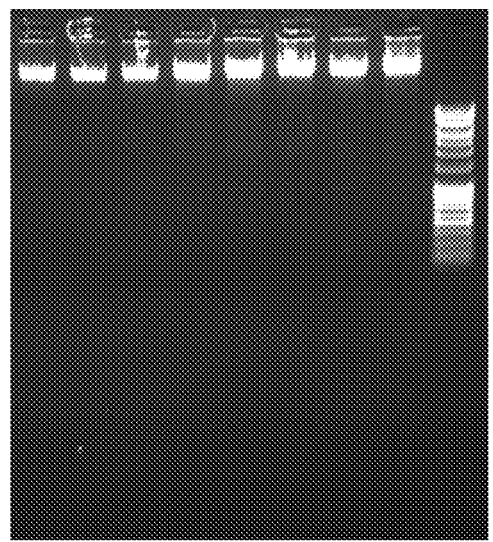
FIG. 2 shows an analysis by gel electrophoresis of the isolated nucleic acid for Example 2.

An analysis by gel electrophoresis of the isolated nucleic acid is shown in FIG. 2.

The nucleic acid separated by electrophoresis in an 0.8% agarose gel is shown which has been isolated by means of the method according to the invention. The samples have been plotted from left to right, starting with sample 1. Track 9 contains a DNA conductor.

Example 3: Concentration of Nucleated Cells from Whole Blood Samples Combined with Subsequent Extraction of the Nucleic Acid Contained in the Nucleated Cells by Using Three Differently Modified Pipette Tips as Well as by Using a Commercially Available Automated Extraction System Automated extraction has again been carried out by the InnuPure C16 (Analytik Jena AG) automated extraction system. For carrying out a nucleic acid extraction pursuant to the method according to the invention, the pipette tips have been modified in such a manner that they correspond to the means according to the invention. For this purpose, the pipette tips have been modified as follows:
1. Pipette tips in the lower third vertically filled loosely with napped plastic granules made of polypropylene (4 granules with a diameter of approx. 2 mm to 4 mm)
2. Pipette tips in the lower third vertically filled loosely with napped plastic granules made of polypropylene (5 granules with a diameter of approx. 2 mm to 4 mm)
3. Pipette tips in the lower third vertically filled with a spiral-shaped plastic material made of polyethylene of a length of 1.5 cm (as an example for a structured material).

The materials were loosely within the pipette tip so that the pipetting function of the pipette tips was entirely maintained. The liquids to be pipetted always moved past the material according to the invention.

The method according to the invention has then been realised on the automated InnuPure C16 system as follows:

The reagents required for the method existed in a pre-filled deepwell plate. A whole blood sample (500 µl) has been put into the first cavity of the deepwell plate. 800 µl each of a commercially available erythrocytes lysis buffer (Ery Lysis Solution A; Analytik Jena AG) have been added to this blood sample. Moreover, still 200 µl of a 1 M calcium chloride solution were added.

The pipette tip with the material according to the invention has been introduced into the cavity. Cell binding occurred by pipetting and pipetting off (100 repetitions). During this process, the nucleated cells adsorb to the material according to the invention contained in the tip. After termination of the pipetting operation, the tip has been extracted from the cavity. The cells are on the material within the tip. By this, the cells were separated from the actual sample and thus also from inhibitory substances such as hemoglobin. This considerably facilitates the subsequent successful extraction of the nucleic acid. The tip has been subsequently introduced into a second cavity of the deepwell plate. A commercially available lysis buffer as well as proteinase K (LysisSolution CBV; innuPREP Blood DNA Kit/IPC16; Analytik Jena AG) are located in this cavity. Lysis of the cells located on the material occurred by pipetting and pipetting off of the lysis buffer (200 repetitions). The cavity has been heated in addition. At the end of the operation, the released nucleic acid of the cells is in the lysis buffer. The cells are no longer on the material according to the invention. The sample has now been put into the pipette tip and released into another cavity of the deepwell plate. This cavity is pre-filled with an alcohol (isopropanol).

Subsequently, this solution has again been pipetted and pipetted off in such a manner that the solution is flowing past the material filled in (100 repetitions). Now, the binding of the released nucleic acid to the material according to the invention occurred with which the cells had already been adsorbed from the sample before. After binding of the nucleic acid to the granules, the washing steps still occurred.

For this, 3 further cavities of the deepwell plate have been filled with an alcoholic washing buffer. Washing occurred by pipetting and pipetting off of the washing buffers (10 repetitions each time).

After the last washing step, the tip according to the invention and the material contained therein has been dried by pipetting air and thus the remaining ethanol has been removed. Elution of the nucleic acids from the granules occurred in another cavity of the deepwell plate in which 200 µl of water were contained as an eluent. The nucleic acid has been detached from the granules by pipetting and pipetting off of the water (120 repetitions).

Proof of the isolated nucleic acid occurred by means of spectrophotometric measurement and gel electrophoresis. It turns out that by the increase of the blood quantity also the yield of nucleic acid increases. Thus, the method is also excellently suitable for processing larger sample volumes.

Results of the Spectrophotometric Measurement

| Sample | Concentration (ng/µl) | Yield (µg) | Ratio $A_{260}:A_{280}$ | Ratio $A_{260}:A_{230}$ |
|---|---|---|---|---|
| Pipette tip type 1 | 92.5 | 18.5 | 1.8 | 2.1 |
| Pipette tip type 1 | 40 | 8 | 1.7 | 2.1 |
| Pipette tip type 1 | 41.5 | 8.3 | 1.7 | 2.0 |
| Pipette tip type 2 | 89 | 17.8 | 1.8 | 2.0 |
| Pipette tip type 2 | 85 | 17 | 1.8 | 1.8 |
| Pipette tip type 2 | 94.5 | 18.9 | 1.8 | 2.1 |
| Pipette tip type 3 | 63 | 12.6 | 1.8 | 1.8 |
| Pipette tip type 3 | 45.5 | 9.1 | 1.7 | 1.8 |
| Pipette tip type 3 | 41 | 8.2 | 1.7 | 1.7 |

Figure 3:
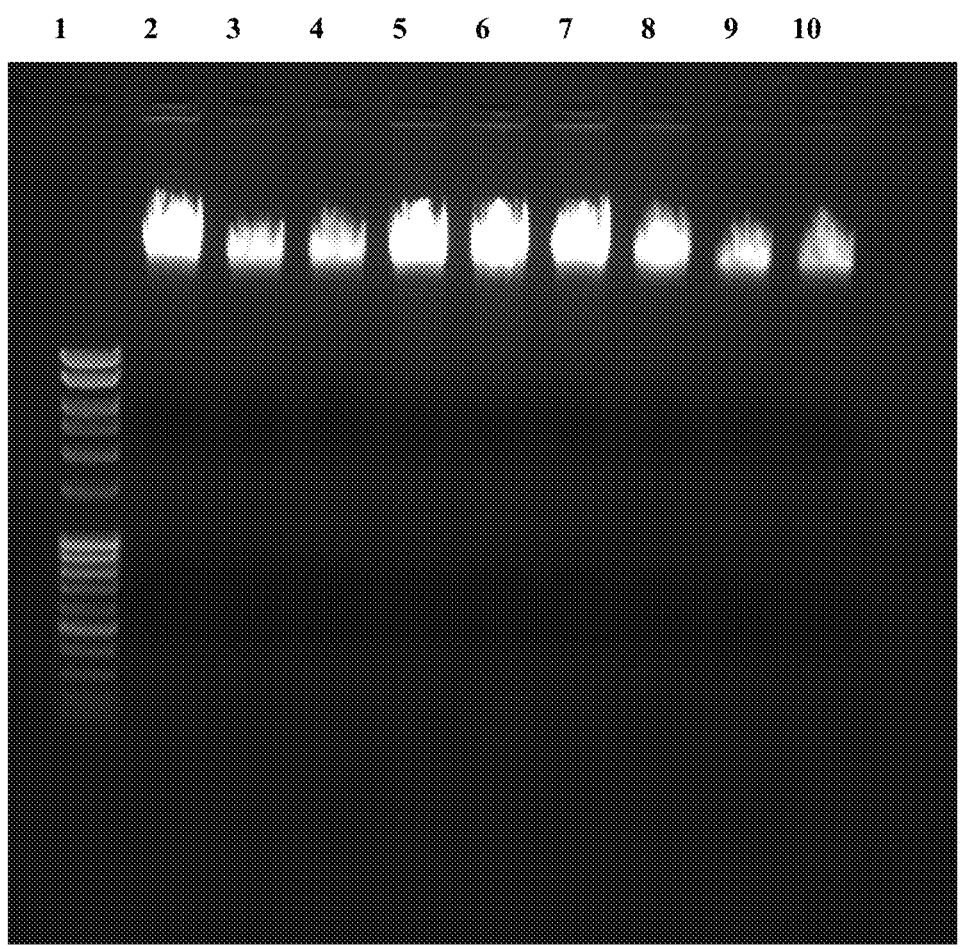
FIG. 3 shows an analysis by gel electrophoresis of the isolated nucleic acid for Example 3.

FIG. 3 shows an analysis by gel electrophoresis of the isolated nucleic acid.

The nucleic acid separated by electrophoresis in an 0.8% agarose gel is shown which has been isolated by means of the method according to the invention. The samples have been plotted from left to right, starting with sample 1. Track 1 contains a DNA conductor.

The invention claimed is:

1. A method for concentrating and isolating biological cells from a sample, comprising:
   contacting a solid phase having a rough and/or structured surface with the sample by placing the solid phase into a cavity containing the sample;
   agitating and/or aspirating the sample with the solid phase having the rough and/or structured surface to adsorb the biological cells onto the solid phase.
2. The method according to claim 1, further comprising:
   adding a salt of a divalent or trivalent cation to the sample prior to the contacting.
3. The method according to claim 2, wherein the salt is calcium chloride.
4. The method according to claim 1, wherein the rough and/or structured surface is a non-smooth plastic surface or rubber surface.
5. The method according to claim 4, wherein the non-smooth plastic surface is created by a 3D print or by roughening of a plastic material.
6. The method according to claim 1, wherein the solid phase comprises a rough composite material.
7. The method according to claim 1, wherein the solid phase comprises a roughened pipette tip.

8. The method according to claim 7, wherein the roughened pipette tip has a magnetic or paramagnetic property.

9. The method according to claim 1, wherein the solid phase with the rough and/or structured surface is introduced into or put onto a smooth hollow body.

10. The method according to claim 9, wherein the solid phase with the rough and/or structured surface is a ring or a sleeve and the smooth hollow body is a pipette tip.

11. A method for concentrating biological cells from a sample and for subsequently isolating nucleic acid from the biological cells, comprising:
   a) contacting a solid phase having a rough and/or structured surface with the sample by placing the solid phase into a cavity containing the sample to adsorb the biological cells onto the solid phase,
   b) lysing the biological cells,
   c) binding the nucleic acid from the biological cells released by the lysing to the solid phase,
   d) optionally, washing and subsequently drying the solid phase, and
   e) finally detaching the nucleic acid from the solid phase with an elution buffer.

12. The method according to claim 11, wherein the method is carried out:
   a. manually or fully automatically as a single tube process, or
   b. as an automated walk-away method.

13. The method according to claim 11, wherein the elution buffer is a low salt buffer or water.

\* \* \* \* \*